United States Patent
Greene et al.

(10) Patent No.: US 7,011,642 B2
(45) Date of Patent: Mar. 14, 2006

(54) EXTERNAL FIXATION DEVICE FOR CRANIALMAXILLOFACIAL DISTRACTION

(75) Inventors: Michael T. Greene, Jacksonville, FL (US); Thomas S. Johnson, Jacksonville, FL (US)

(73) Assignee: KLS-Martin, L.P., Jacksonville, FL (US)

( * ) Notice: Subject to any disclaimer, the term of this patent is extended or adjusted under 35 U.S.C. 154(b) by 215 days.

(21) Appl. No.: 10/667,751

(22) Filed: Sep. 22, 2003

(65) Prior Publication Data

US 2004/0199094 A1 Oct. 7, 2004

Related U.S. Application Data

(60) Provisional application No. 60/460,941, filed on Apr. 7, 2003.

(51) Int. Cl.
*A61F 5/00* (2006.01)
(52) U.S. Cl. ............................. 602/36; 602/32; 433/18; 128/845
(58) Field of Classification Search ............ 602/17–18, 602/32, 36, 74; 433/5; 128/97.1, 845, 857, 128/859; 600/590; 601/38; 482/11
See application file for complete search history.

(56) References Cited

U.S. PATENT DOCUMENTS

| 678,417 A | 7/1901 | Muller | |
|---|---|---|---|
| 1,301,276 A | 4/1919 | Kroetz | |
| 2,151,458 A * | 3/1939 | Allen | 602/17 |
| 2,325,300 A * | 7/1943 | Bisnoff | 602/17 |
| 2,334,894 A * | 11/1943 | Atkinson | 433/5 |
| 2,360,738 A * | 10/1944 | Stevenson | 602/17 |
| 2,371,197 A * | 3/1945 | Taylor | 602/17 |
| 2,453,934 A * | 11/1948 | Preston | 602/17 |
| 2,672,146 A | 3/1954 | Touson | |
| 2,681,058 A * | 6/1954 | Mathues | 602/17 |
| 3,072,118 A | 1/1963 | Standerwick et al. | |
| 3,391,693 A * | 7/1968 | Georgiade et al. | 602/17 |
| 3,900,896 A | 8/1975 | Ackerman | |
| 3,957,040 A | 5/1976 | Calabrese | |
| 4,259,065 A * | 3/1981 | DeWoskin | 433/5 |
| 4,375,962 A * | 3/1983 | DeWoskin | 433/5 |
| 5,094,229 A | 3/1992 | Pomatto et al. | |
| 5,581,820 A | 12/1996 | Cartwright et al. | |
| 5,890,891 A * | 4/1999 | Doyle | 433/5 |
| 6,213,765 B1 * | 4/2001 | Standerwick et al. | 433/5 |
| 6,423,019 B1 * | 7/2002 | Papay et al. | 602/17 |
| 6,428,494 B1 | 8/2002 | Schwenn et al. | |

OTHER PUBLICATIONS

KLS Martin, L.P.—Rigid External Distraction Red II System brochure.
W. Lorenz BlueDevice Multi-Vector Distraction brochure.

* cited by examiner

*Primary Examiner*—Henry Bennett
*Assistant Examiner*—Amanda Wieker
(74) *Attorney, Agent, or Firm*—Thomas C. Saitta

(57) ABSTRACT

An externally mounted fixation device for craniomaxillofacial distraction osteogenesis, the device having a helmet to secure the device in a relatively rigid and immobile manner to the head of a patient, support structure to receive distraction components in fixed or adjustable spatial location relative to the patient's head, and distraction components to apply traction to the bones of the patient to be distracted.

49 Claims, 5 Drawing Sheets

EXTERNAL FIXATION DEVICE FOR CRANIALMAXILLOFACIAL DISTRACTION

This application claims the benefit of U.S. Provisional Patent Application Ser. No. 60/460,941, filed Apr. 7, 2003.

BACKGROUND OF THE INVENTION

This invention relates generally to the field of craniomaxillofacial distraction osteogenesis devices for treatment of craniofacial anomalies wherein a distractive force is to applied to portions of the craniofacial skeleton, mandible or maxila of a patient, the device being worn by the patient for an extended period of time such that relatively minor adjustments may be made in order to gradually effect osteogenesis.

Prior art fixation devices directed at the treatment of craniofacial anomalies, LeFort I mid-face asymmetry, maxillary and mid-face skeletal hypoplasia, mandibular hypoplasia, and similar conditions through distraction osteogenesis are known, the common such device being referred to as a halo fixation or distraction device. The term halo comes from the generally ring-shaped or U-shaped frame member that is fixated about the head of the patient. The halo is mounted to the head by a plurality of fixation screws that are tightened against the skull of the patient. The halo thus provides a support framework to which are attached the distraction means. While this method is effective in providing a fixed mounting of the device to the patient where relative movement between the halo and the patient's head in precluded, with relatively low pain and discomfort from the fixation screws, in young patients or with certain conditions the bone may not be strong enough to use fixation screws or cranial pins. Where internal bone fixation means are utilized, a second operation to remove the distraction apparatus is required. In addition, the visual presentation of the halo device is not pleasing.

It is an object of this invention to provide a craniomaxillofacial distraction osteogenesis device wherein the inherent problems associated with the halo devices are obviated by providing head mounting means for supporting the distraction means that does not utilize a ring-like or U-shaped frame mounted onto the head of a patient by fixation screws or pins, wherein instead the head mounting means comprises a helmet-type device, whether a full helmet, an open-top helmet, a shell or a cranial band, such that the compressive forces necessary to retain the helmet and the device on the patient's head in a fixed manner are broadly distributed about the head of the patient. It is a further object to provide such a device wherein the helmet is adjustable in configuration for size, shape and comfort, or wherein the helmet can be custom fitted to match the configuration of the patient's head. It is a further object to provide such a device wherein the distraction means can be attached to the helmet mid-face, laterally over the temporal or mandible area, or at other desired locations. These objects, in addition to objects not expressly stated here, are achieved by providing a device as disclosed below.

SUMMARY OF THE INVENTION

The invention is an externally mounted fixation device for craniomaxillofacial distraction osteogenesis, the device comprising in general mounting means to secure the device to the head of a patient, support means to receive distraction components in fixed spatial location relative to the patient's head, and distraction means to apply traction to the bones of the patient to be distracted.

The mounting means to secure the device to the head of the patient comprises a helmet-type member, either a full or partial helmet, a shell or a cranial band composed of a relatively rigid material, corresponding generally in shape and configuration to the head of the patient and covering to some extent the frontal, occipital and temporal regions, preferably with the top of the head and the ear region exposed. Preferably, the head mounting means is provided with size, shape and comfort adjustment means, such as by providing a vertical slit and closure means, or by providing a compressible inner liner, or by providing interior bladder or shaping elements. The head mounting means may be produced in incremental sizes, but is preferably custom manufactured based on measurements of the particular patient. The head mounting means sufficiently envelopes the patient's head in a manner that results in a fixed and stable mounting, such that there is at most limited or negligible movement of the device relative to the patient's head when the device is secured in place.

The support means to receive the distraction components in fixed spatial location relative to the patient's head comprises either an anterior mounting member for securing an elongated support rod to the anterior portion of the head mounting means, such that the support rod is generally vertically disposed when the device is in place on the patient, with the support rod positioned outwardly a short distance in front of the patient's face, or a temporal mounting member for securing an elongated temporal support rod or rods to the temporal portion of the head mounting means, on one or both sides, such that the support rod is angled from vertical or even horizontally disposed. Preferably the mounting member allows the support rod or rods to be oriented at various angles and/or various vertical positions relative to the helmet so as to allow for adjustment of the distraction vector, such as by providing a locking universal joint or a rotational mechanism. One or more crossbar assemblies are connected to or mounted on the vertical support rod, preferably in a manner that allows the position of the crossbar assembly to be adjusted as required, the crossbar assembly typically comprising a crossbar rod disposed generally perpendicularly to the vertical bar such that the crossbar rod is generally horizontally disposed when the device is in place on the patient. The crossbar rod is adapted to receive the distraction means.

The distraction means comprises any distraction assembly whereby traction or distraction can be applied to the particular bones and locations desired to be distracted into an altered final position and configuration. A typical distraction assembly comprises bone attachment means, such as for example bone plates and bone screws secured to portions of the skull or intraoral wire splints secured about the teeth to form external traction hooks, distraction screws connected to the bone attachment means by wire or similar means, and spindle housings retaining the distraction screws, the spindle housings being preferably adjustably mounted onto the crossbar rod. Rotation of the distraction screws in the proper direction results in linear distraction movement relative to the spindle housing and support means, such that the bone attachment means and the associated portions of the skull are pulled forward. For the temporal support rod or rods, the distraction means may be connected directly thereto, or additional mounting components may be provided.

DETAILED DESCRIPTION OF THE INVENTION

With reference to the drawings, the invention will now be described in detail with regard for the best mode and the preferred embodiment. In general, the invention is a craniomaxillofacial distraction osteogenesis apparatus or device as shown in FIGS. 2 through 6, the device being suitable for treatment of craniofacial anomalies, LeFort I mid-face asymmetry, maxillary and mid-face skeletal hypoplasia, mandibular hypoplasia and similar conditions. The device delivers controlled rigid distraction forces, allows multi-directional distraction, allows for multiplanar adjustability of distraction forces at any time during the distraction procedure, is easily and quickly placed at the time of osteotomy, is easily and quickly removed in an office or clinical setting. The device is suitable for patients who are unsuitable for conventional orthognathic surgery or for treatment with a halo appliance.

Figure 1:
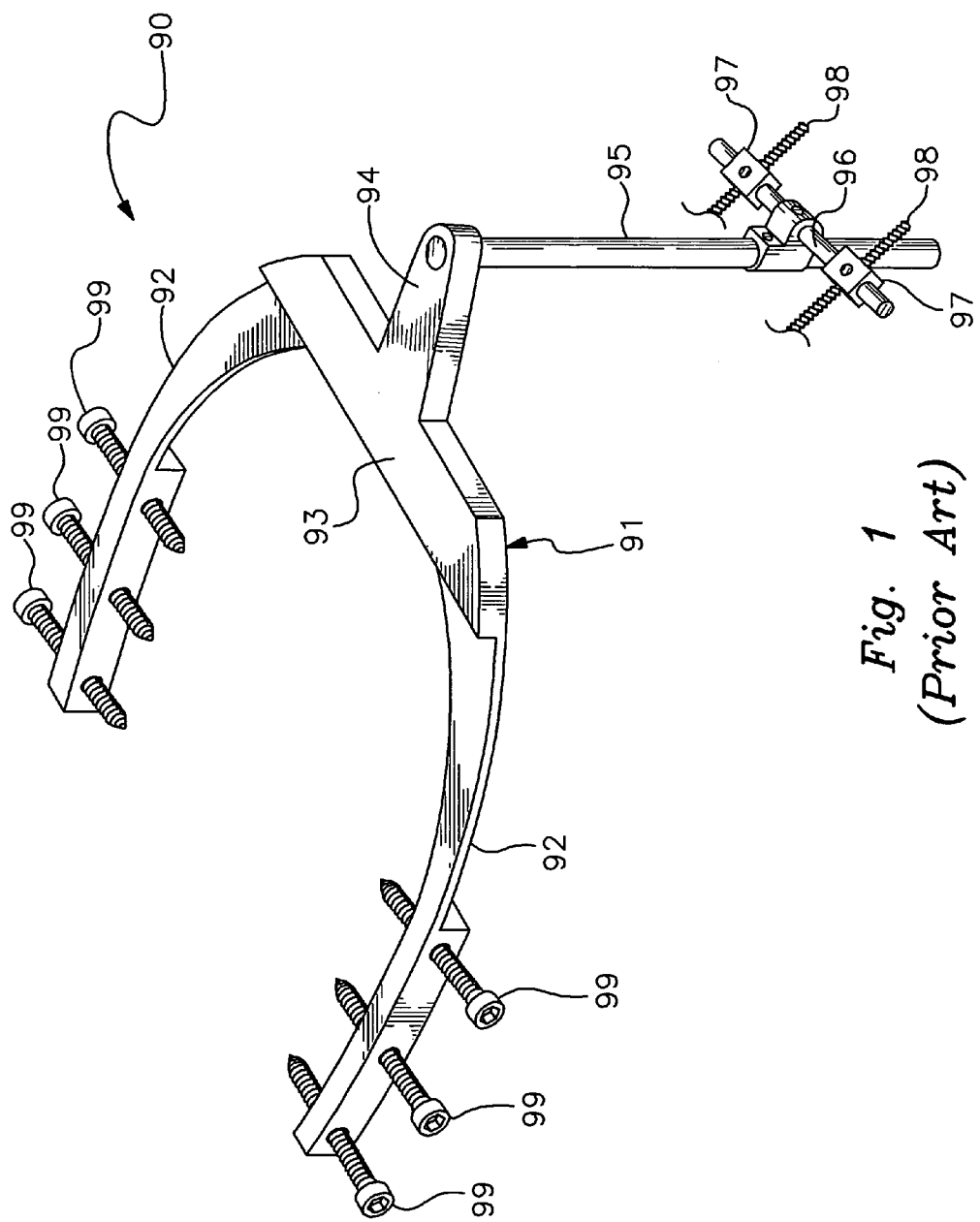
FIG. 1 shows a prior art halo device.

A prior art device 90 of the type commonly referred to as a halo device is depicted in FIG. 1, which shows a generally U-shaped halo mounting member 91 comprising a pair of arm members 92 extending posteriorly from an anterior bridge member 93. An anterior stem member 94 retains a vertically oriented support bar member 95, to which is mounted a horizontally oriented crossbar member 96. A pair of distraction assemblies 97 are mounted onto the crossbar member 96, each distraction assembly 97 comprising a distraction screw member 98. A plurality of fixation screw members 99 is disposed on each of the arms 92. To secure this prior art device 90 to a patient's head, the halo mounting member 91 is properly positioned by the surgeon and the fixation screw members 99 are advanced against the patient's skull with sufficient pressure such that the device 99 remains in fixed relation to the patient's head.

In contrast, the craniomaxillofacial distraction device 10 comprises the combination of head mounting means 20, support means 40 and distraction means 60, wherein the head mounting means 20 does not include fixation screws or similar discrete, high-force contact mechanisms. The head mounting means 20 instead comprises a structure that secures the device 10 to the patient's head 100 in a fixed manner such that significant relative motion does not occur between the device 10 and the patient's head 100, wherein the compressive forces are spread out or distributed such that localized pressure points are avoided. The head mounting means 20 is preferably composed of relatively rigid polymer material, such that relatively minimal flex and compression are present, especially when the head mounting means 20 is in use on the patient. The head mounting means 20 comprises a helmet, shell or cranial band, to be referred to herein collectively as a helmet 21. The helmet 21 is shaped to closely mate with the head 100 of the patient, such that portions of the frontal, occipital and temporal regions are covered and encased, with the posterior portion 34 typically being of greater vertical dimension than the anterior portion 33. Although the helmet 21 may be provided in incremental sizes, it is most preferable that the helmet 21 be custom fitted to the particular patient, such that inconsistencies in the shape or configuration of the head 100 are replicated in the shape and configuration of the helmet 21. Most preferably, the top portion of the helmet 21 comprises an upper edge 22 defining a relatively large open area, thereby allowing body heat to escape as well as providing access to the hair and scalp for cleaning purposes, although it is possible to provide a helmet 21 having apertures or one where the hair and scalp are fully enclosed. Also most preferably, the helmet 21 is shaped such that the ears are not encased.

Figure 2:
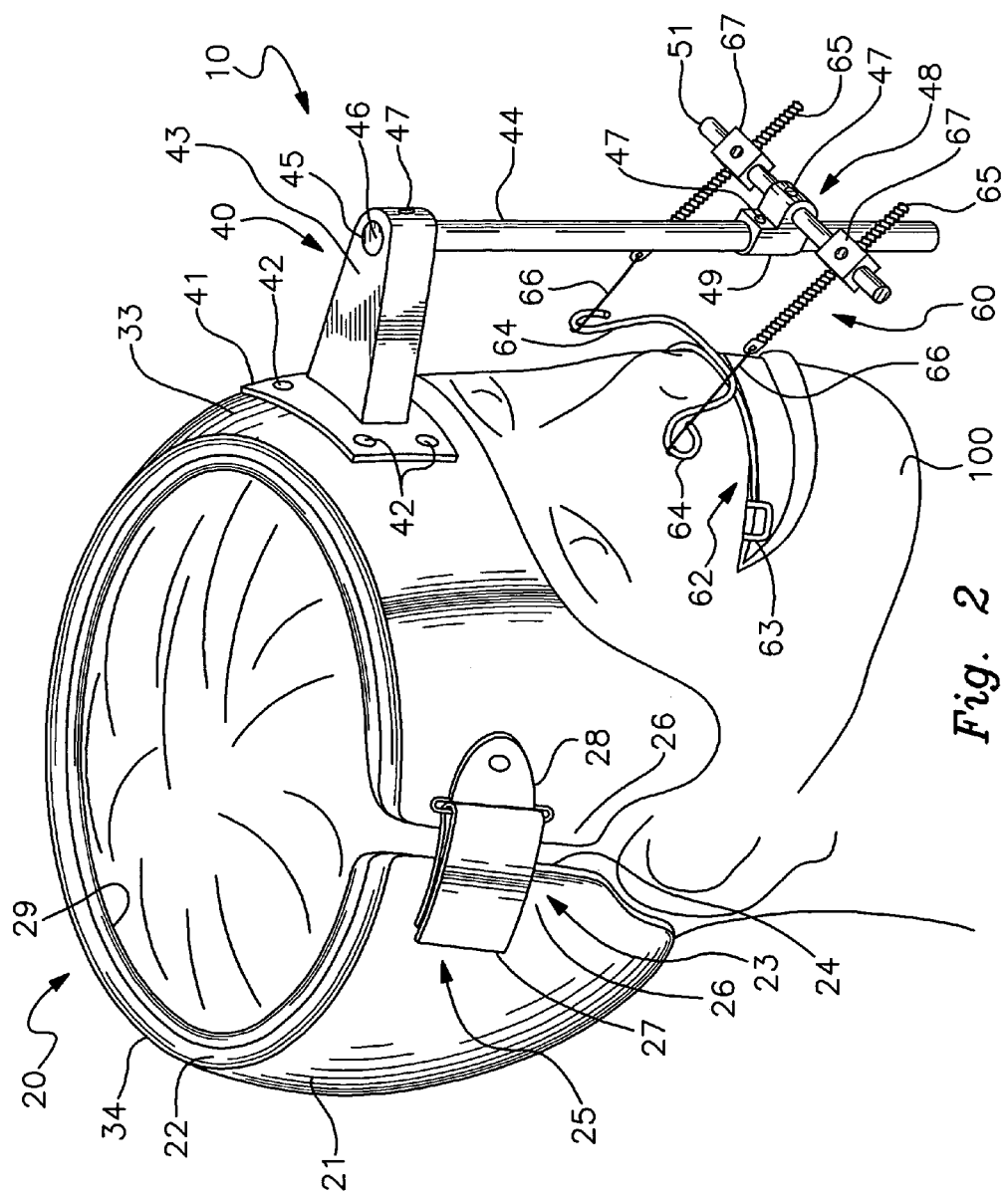
FIG. 2 is a perspective view of the invention shown mounted onto a patient's head, wherein the support means for the distraction means is mounted to the anterior portion of the helmet.
Figure 3:
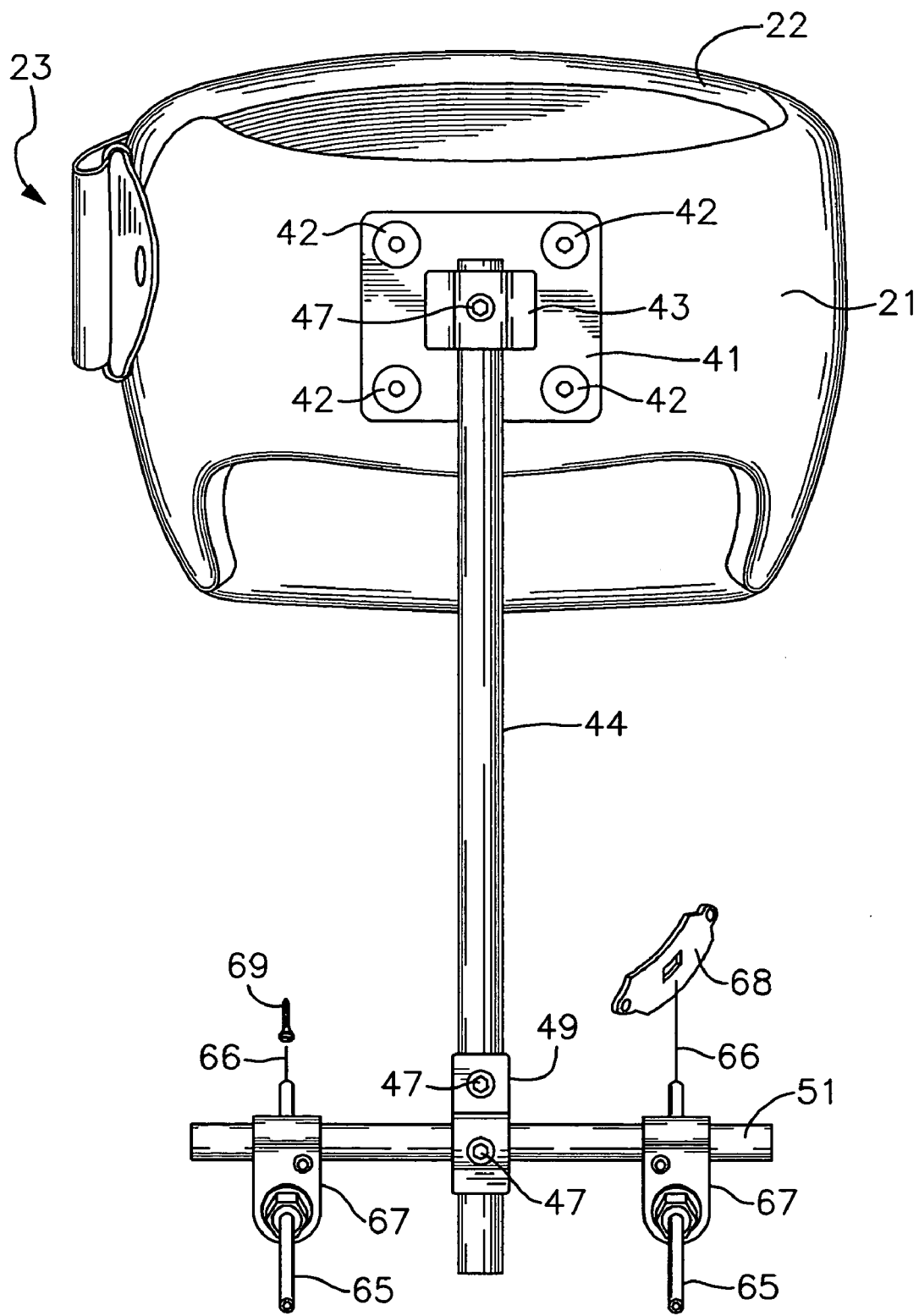
FIG. 3 is a front view of the invention as shown in FIG. 2, with a partial view of the distraction means.
Figure 4:
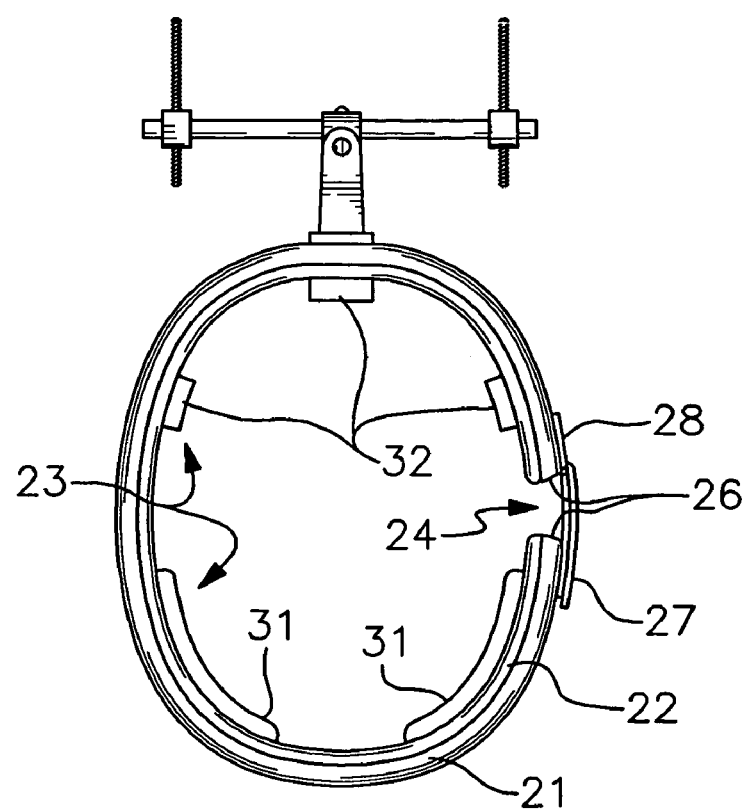
FIG. 4 is a top view of the invention as shown in FIG. 2, with a partial view of the distraction means.

The helmet 21 may be provided with adjustment means 23 to alter the configuration of the helmet 21, such as in size, shape and comfort. For example, the adjustment means 23 may comprise a generally vertical slit 24 extending completely through one or both sides of the helmet 21, with closure means 25 provided to secure the two ends 26 of the helmet 21 in a fixed relationship. The closure means 25 may comprise for example a hook and loop type fastener 27 threaded through a buckle 28, where the buckle 28 is mounted on one end 26 and the hook and loop type fastener is affixed to the other end 26. The closure means 25 may comprise other equivalent mechanisms, such as apertured straps, mechanical clasps, threaded bolts, or the like. Furthermore, adjustment means 23 may comprise internally disposed members such as a compressible liner 29, as shown in FIG. 2, or as shown in FIG. 4, inflatable bladders 31 or shaping members 32 made of a relatively dense material.

Figure 7:
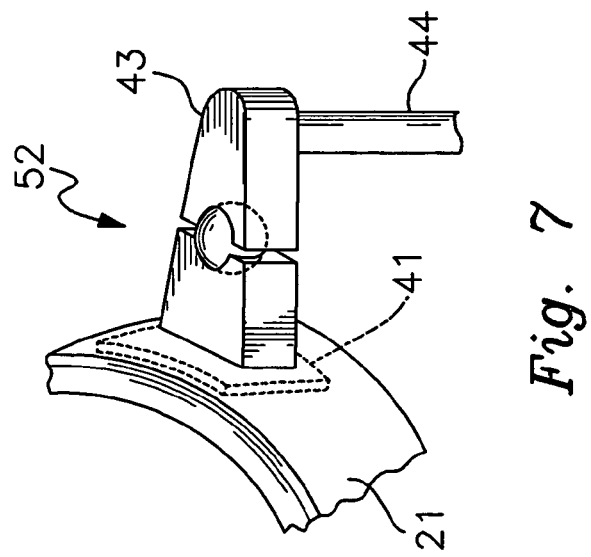
FIG. 7 is a perspective view of an anterior mounting member comprising a universal joint mechanism.

In a first embodiment, the anterior portion 33 of the helmet 21 that is disposed on the patient's forehead is adapted to rigidly and securely receive the support means 40 for the distraction means 60. The support means 40 may comprise any suitable frame or mounting structure suitable to be secured to the helmet 21 such that the distraction means 60 may be fixedly disposed at the proper location relative to the patient's head 100. As illustrated, a preferred embodiment for support means 40 comprises an anterior mounting member 41 comprising a plate contoured to mate with the anterior portion 33 of the helmet 21, being secured thereto with mechanical fasteners 42, adhesive or equivalent means, from which extends a mounting stem 43. Most preferably, the anterior mounting member 41 is embedded within the anterior portion 33 of helmet 21, in which case mechanical fasteners 42 may not be required. Mounting stem 43 may also incorporate a multi-directional orientation means 52, as shown in FIG. 7, such as a universal joint, socket and ball assembly, paired spline gears or the like, that allows the orientation of the distal end of the mounting stem 43 to be altered as required. Depending from the mounting stem 43 in a generally vertical orientation is an elongated vertical support rod or brace member 44. The vertical rod member 44 may be adjustable relative to the mounting stem 43, such as by providing a bore 45 to receive the upper end 46 of the vertical support rod member 44, with a set screw 47 provided to secure the vertical support rod member 44 in the desired position. The mounting stem 43 extends forward from the anterior portion 33 of the helmet 21, such that the vertical support rod member 44 is located a short distance, typically about one to three inches, in front of the patient's head 100.

One or more crossbar assemblies 48 are mounted generally perpendicularly onto the vertical support rod member 44. Preferably the crossbar assembly 48 is provided with a mounting bracket 49 that allows the position of the crossbar assembly 48 on the vertical support rod member 44 to be adjusted, by use of a set screw 47 for example, both as to vertical position along the vertical support rod member 44 and angularly relative to the patient's head 100. Likewise, the mounting bracket 49 may be structured to receive the crossbar rod member 51 in an adjustable manner, by use of set screw 47 for example, such that the crossbar rod member 51 may be moved transversely relative to the vertical support rod member 44.

The distraction means 60 are mounted onto the crossbar rod member 51, typically one to each side of the vertical support rod member 44. Distraction means 60 may comprise any type of distraction assembly known or equivalent to the known distraction assemblies in purpose and function, whereby a traction or distracting force can be applied to particular bones or bone segments such that the configuration of the bones in the skull or jaw is altered over time. The embodiment as illustrated comprises a pair of distraction assemblies 61 each comprising bone attachment means 62, such as for example bone plates 68 and/or bone screws 69 secured to portions of the skull or jaw or, as shown, intraoral wire splints 63 secured about the teeth to form external traction hook members 64, threaded distraction screws 65 connected to the bone attachment means 62 by wires 66 or similar means, and spindle housings 67 with internally threaded bores to receive and retain the distraction screws 65. The spindle housings 67 are preferably adjustably disposed on the crossbar rod 51 such that lateral positioning is achievable. In this manner, rotation of the distraction screws 65 in the proper direction results in linear distraction movement of the distraction screws 65, wires 66 and bone attachment means 62, due to the fixed spatial relationship of the support means 40 relative to the patient's head 100.

Figure 5:
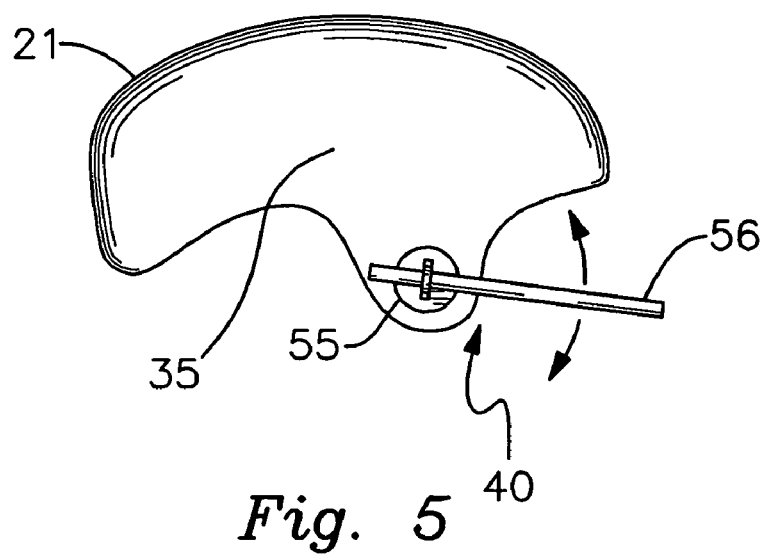
FIG. 5 is a side view of an alternative embodiment of the invention, wherein the support means is mounted onto the temporal portion of the helmet.
Figure 8:
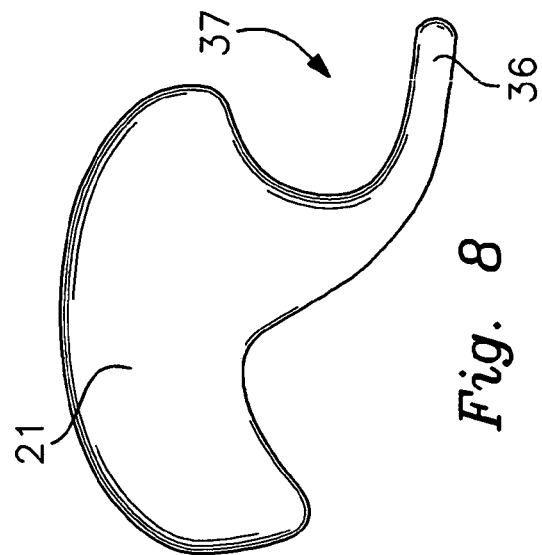
FIG. 8 is a side view of a helmet comprising a chin member for support of the distraction means.
Figure 6:
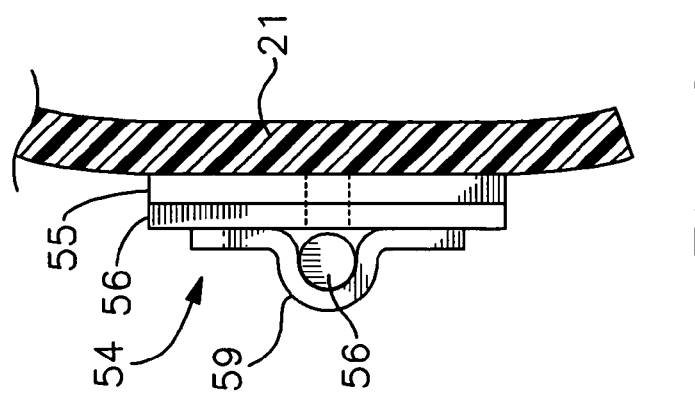
FIG. 6 is a front view of the rotating temporal mount of the invention as shown in FIG. 5.

In an alternative embodiment shown in FIGS. 5 and 6, wherein the head mounting means 20 is illustrated as a full helmet 21, the support means 40 comprises at least one, but typically an opposing pair of temporal mounting members 55 positioned on the lateral or temporal portion 35 of the helmet 21 such that the support rod 56 which receives the distraction means 60 is positioned generally horizontally or at a non-vertical angle along the temporal or mandibular side of the patient. Preferably, the support means 40 is adjustable relative to the helmet 21 through temporal orientation means 54, such that the angle of the support rod 56 relative to horizontal can be altered as required. As shown in FIG. 6, temporal orientation means 54 may comprise for example a rotating plate member 57 attached by a pivoting connector means 58 to temporal mounting member 55, with support rod 56 attached to the rotating plate member 57 by a bracket 59 or similar attachment means.

In a further alternate embodiment, the helmet 21 may comprise a chin member 36 such that a face opening 37 is defined, the helmet 21 being similar in appearance to full face helmets worn for example by motorcyclists, ski racers or downhill mountain bikers. Suitable support means 40 is then provided if necessary as generally described above, and the distraction means 60 are then mounted to the support means 40 or to the chin member 36 itself.

It is understood that equivalents and substitutions for certain elements and structure set forth above may be known or obvious to those skilled in the art, and thus the true scope and definition of the invention is to be as set forth in the following claims.

We claim:

1. A craniomaxillofacial distraction device comprising:
   head mounting means for securing said device to the head of a patient in a fixed manner, said head mounting means comprising a helmet composed of a rigid material and having for altering the configuration of said helmet while in the rigid state, wherein said helmet distributes compressive forces such that localized pressure points are avoided;
   support means for receiving distraction means, said support means being connected to said head mounting means; and
   distraction means for applying distracting forces to treat craniofacial anomalies, said distraction means being mounted onto said support means.

2. The device of claim 1, wherein said support means comprises a generally vertically oriented support rod member.

3. The device of claim 2, wherein said support means further comprises an anterior mounting member secured to said helmet.

4. The device of claim 3, wherein said support means further comprises a mounting stem extending from said anterior mounting member, said support rod member being connected to said mounting stem.

5. The device of claim 2, wherein said support means further comprises a crossbar assembly comprising a generally horizontally disposed crossbar rod member.

6. The device of claim 5, wherein said crossbar assembly is adjustable relative to said support rod member.

7. The device of claim 2, wherein said support means further comprises multi-directional orientation means, such that the orientation of said vertically oriented support rod member is adjustable relative to said head mounting means.

8. The device of claim 7, wherein said multi-directional orientation means comprises a universal joint.

9. The device of claim 1, wherein said helmet is composed of a polymer material.

10. The device of claim 1, wherein said helmet is custom fitted to correspond directly to the head of said patient.

11. The device of claim 1, wherein said helmet is open on the top.

12. The device of claim 1, wherein said adjustment means comprises a generally vertical slit defining ends on said helmet, and closure means for securing said ends.

13. The device of claim 1, wherein said adjustment means comprises an internally disposed compressible liner.

14. The device of claim 1, wherein said adjustment means comprises inflatable bladders.

15. The device of claim 1, wherein said adjustment means comprises internally disposed shaping members.

16. The device of claim 1, wherein said support means comprises a temporal mounting member secured directly to said helmet.

17. The device of claim 16, wherein said support means further comprises a non-vertically oriented support rod member connected to said temporal mounting member.

18. The device of claim 17, wherein said support means further comprises temporal orientation means, such that the orientation of said non-vertically oriented support rod member is adjustable relative to said head mounting means.

19. The device of claim 17, wherein said temporal orientation means comprises a rotating plate member pivotally attached to said temporal mounting member and wherein said non-vertically oriented support rod member is connected to said temporal mounting member through said rotating plate member.

20. A craniomaxillofacial distraction device comprising:
head mounting means for securing said device to the head of a patient in a fixed manner, said head mounting means comprising a helmet, wherein said helmet distributes compressive forces such that localized pressure points are avoided;
support means for receiving distraction means, said support means being connected to said head mounting means; and
distraction means for applying distracting forces to treat craniofacial anomalies, said distraction means being mounted onto said support means, wherein said distraction means comprises a pair of distraction assemblies each comprising a threaded distraction screw, a spindle housing to receive said distraction screw, and a bone attachment means.

21. The device of claim 20, wherein said bone attachment means comprises a bone plate.

22. The device of claim 20, wherein said bone attachment means comprises a bone screw.

23. The device of claim 20, wherein said bone attachment means comprises an intraoral wire.

24. A craniomaxillofacial distraction device for treating craniofacial anomalies in the jaw of a patient comprising:
head mounting means for securing said device to the head of the patient in a relatively fixed manner wherein relative motion between said head mounting means and the head of the patient is limited, said head mounting means comprising a helmet composed of a rigid material and having adjustment means and having adjustments for altering the configuration of said helmet while in the rigid state, wherein said helmet distributes compressive forces such that localized pressure points are avoided;
support means for receiving distraction means, said support means being connected to said head mounting means;
distraction means for applying distraction forces to the jaw of the patient, said distraction means being mounted onto said support means and comprising at least a pair of distraction assemblies connected to the jaw of said patient.

25. The device of claim 24, wherein said support means comprises a generally vertically oriented support rod member and a generally horizontally oriented crossbar rod member.

26. The device of claim 25, wherein said support means further comprises an anterior mounting member secured directly to said helmet and a mounting stem extending from said anterior mounting member, said support rod member being connected to said mounting stem.

27. The device of claim 25, wherein said crossbar rod member is adjustable relative to said support rod member.

28. The device of claim 25, wherein said support means comprises multi-directional orientation means, such that the orientation of said vertically oriented support rod member relative to said head mounting means may be altered.

29. The device of claim 28, wherein said multi-directional orientation means comprises a universal joint.

30. The device of claim 24, wherein said helmet is composed of a polymer material.

31. The device of claim 24, wherein said helmet is custom fitted to correspond directly to the head of said patient.

32. The device of claim 24, wherein said helmet is open on the top.

33. The device of claim 24, wherein said adjustment means comprises a generally vertical slit defining ends on said helmet, and closure means for securing said ends.

34. The device of claim 24, wherein said adjustment means comprises an internally disposed compressible liner.

35. The device of claim 24, wherein said adjustment means comprises inflatable bladders.

36. The device of claim 24, wherein said adjustment means comprises internally disposed shaping members.

37. The device of claim 24, wherein said support means comprises at least one temporal mounting member secured directly to said helmet.

38. The device of claim 37, wherein said support means further comprises a non-vertically oriented support rod member connected to said at least one temporal mounting member.

39. The device of claim 38, wherein said support means further comprises temporal orientation means, such that the orientation of said non-vertically oriented support rod member is adjustable relative to said head mounting means.

40. The device of claim 39, wherein said temporal orientation means comprises a rotating plate member pivotally attached to said at least one temporal mounting member.

41. The device of claim 40, wherein said support means comprises a temporal mounting member secured directly to said helmet and a non-vertically oriented support rod member connected to said temporal mounting member.

42. A craniomaxillofacial distraction device for treating craniofacial anomalies in the jaw of a patient comprising:
head mounting means for securing said device to the head of the patient in a relatively fixed manner wherein relative motion between said head mounting means and the head of the patient is limited, said head mounting means comprising a helmet, wherein said helmet distributes compressive forces such that localized pressure points are avoided;
support means for receiving distraction means, said support means being connected to said head mounting means;
distraction means for applying distraction forces to the jaw of the patient, said distraction means being mounted onto said support means and comprising at least a pair of distraction assemblies connected to the jaw of said patient, wherein said distraction means comprises a pair of distraction assemblies each comprising a threaded distraction screw, a spindle housing to receive said distraction screw, and a bone attachment means for connecting said distraction screw to the jaw of the patient.

43. The device of claim 42, wherein said bone attachment means comprises a bone plate.

44. The device of claim 42, wherein said bone attachment means comprises a bone screw.

45. The device of claim 42, wherein said bone attachment means comprises an intraoral wire.

46. A craniomaxillofacial distraction device for treating craniofacial anomalies in the jaw of a patient comprising:
head mounting means for securing said device to the head of the patient in a generally fixed manner wherein relative motion between said head mounting means and the head of the patient is limited, said head mounting means comprising a helmet, wherein said helmet distributes compressive forces such that localized pressure points are avoided, wherein said helmet is composed of a polymer material and comprising adjustment means for altering the configuration of said helmet;

support means for receiving distraction means, said support means being connected to said head mounting means; and distraction means for applying distraction forces to the jaw of the patient, said distraction means being mounted onto said support means and comprising at least a pair of distraction assemblies connected to the jaw of said patient, said distraction assemblies each comprising a threaded distraction screw, a spindle housing to receive said distraction screw, and a bone attachment means for connecting said distraction screw to the jaw of the patient.

47. The device of claim 46, wherein said support means comprises a generally vertically oriented support rod member, a generally horizontally disposed crossbar rod member mounted to said vertically oriented support rod member, an antenor mounting member secured directly to said helmet and a mounting stem extending from said anterior mounting member, said support rod member being connected to said mounting stem, wherein said crossbar rod member is adjustable relative to said support rod member.

48. The device of claim 47, wherein said support means further comprises multi-directional orientation means such that the orientation of said vertically oriented support rod member is adjustable relative to said head mounting means.

49. The device of claim 48, wherein said support means further comprises temporal orientation means, such that the orientation of said non-vertically oriented support rod member is adjustable relative to said head mounting means.

* * * * *

UNITED STATES PATENT AND TRADEMARK OFFICE
CERTIFICATE OF CORRECTION

| | | |
|---|---|---|
| PATENT NO. | : 7,011,642 B2 | Page 1 of 1 |
| APPLICATION NO. | : 10/667751 | |
| DATED | : March 14, 2006 | |
| INVENTOR(S) | : Greene et al. | |

It is certified that error appears in the above-identified patent and that said Letters Patent is hereby corrected as shown below:

<u>Title Page</u>
Item (75)
The correct name of the second-listed inventor is Thomas S. Johnston.

Signed and Sealed this

Fourteenth Day of November, 2006

JON W. DUDAS
*Director of the United States Patent and Trademark Office*